(12) United States Patent
Robnett

(10) Patent No.: US 9,227,052 B2
(45) Date of Patent: Jan. 5, 2016

(54) NEUROSTIMULATOR INTERCONNECTION APPARATUS, SYSTEM, AND METHOD

(71) Applicant: Greatbatch Ltd., Clarence, NY (US)

(72) Inventor: Ronald H. Robnett, Santa Monica, CA (US)

(73) Assignee: Greatbatch Ltd.

(*) Notice: Subject to any disclaimer, the term of this patent is extended or adjusted under 35 U.S.C. 154(b) by 0 days.

(21) Appl. No.: 14/320,676

(22) Filed: Jul. 1, 2014

(65) Prior Publication Data

US 2015/0018912 A1 Jan. 15, 2015

Related U.S. Application Data

(60) Provisional application No. 61/841,965, filed on Jul. 2, 2013.

(51) Int. Cl.

| | |
|---|---|
| *A61N 1/00* | (2006.01) |
| *A61N 1/05* | (2006.01) |
| *A61B 5/06* | (2006.01) |
| *A61B 8/08* | (2006.01) |
| *A61N 1/36* | (2006.01) |
| *A61N 1/372* | (2006.01) |

(52) U.S. Cl.
CPC .............. *A61N 1/0551* (2013.01); *A61B 5/064* (2013.01); *A61B 8/0841* (2013.01); *A61N 1/05* (2013.01); *A61N 1/0553* (2013.01); *A61N 1/36017* (2013.01); *A61N 1/36125* (2013.01); *A61N 1/36139* (2013.01); *A61N 1/36146* (2013.01); *A61N 1/36153* (2013.01); *A61N 1/37223* (2013.01); *A61N 1/37235* (2013.01); *A61N 1/37252* (2013.01)

(58) Field of Classification Search
CPC ........ A61B 5/064; A61B 8/0841; A61N 1/05; A61N 1/0551; A61N 1/0553; A61N 1/36017; A61N 1/36125; A61N 1/36139; A61N 1/36146; A61N 1/36153; A61N 1/3722; A61N 1/37235; A61N 1/37252
See application file for complete search history.

(56) References Cited

U.S. PATENT DOCUMENTS

| | | | |
|---|---|---|---|
| 3,522,575 A | 8/1970 | Johnson et al. | |
| 5,662,696 A | 9/1997 | Kroll et al. | |
| 5,733,151 A * | 3/1998 | Edsall et al. | 439/729 |
| 5,906,634 A | 5/1999 | Flynn et al. | |
| 6,198,969 B1 | 3/2001 | Kuzma | |
| 6,516,227 B1 | 2/2003 | Meadows et al. | |
| 6,609,029 B1 | 8/2003 | Mann et al. | |
| 7,002,131 B1 | 2/2006 | Lewis et al. | |
| 7,526,339 B2 | 4/2009 | Lahti et al. | |
| 7,798,864 B2 * | 9/2010 | Barker et al. | 439/668 |
| 8,100,019 B2 * | 1/2012 | Moldenhauer | 73/721 |
| 8,206,175 B2 | 6/2012 | Boyd et al. | |
| 8,380,310 B2 | 2/2013 | Visco et al. | |

(Continued)

*Primary Examiner* — George Manuel
(74) *Attorney, Agent, or Firm* — Michael P. Horvath

(57) ABSTRACT

In various examples, a neurostimulation interconnection apparatus apparatus includes a substrate disposed within a header of a neurostimulation device. A spring contact is mounted to the substrate. The spring contact is oriented to accept and apply a clamping force to a proximal contact of a lead body to electrically couple the proximal contact of the lead body with the spring contact with insertion of the proximal contact within the spring contact. A trace is disposed on the substrate from the spring contact to a pin of a feedthrough of the neurostimulation device. The trace electrically couples the spring contact with the pin of the feedthrough.

20 Claims, 2 Drawing Sheets

(56) References Cited

U.S. PATENT DOCUMENTS

| | | |
|---|---|---|
| 8,401,649 B2 | 3/2013 | Tronnes et al. |
| 8,433,410 B2 | 4/2013 | Dabney et al. |
| 8,587,427 B2 | 11/2013 | Lalonde et al. |
| 8,639,354 B2 | 1/2014 | Bolea et al. |
| 8,700,160 B2 | 4/2014 | Berthin et al. |
| 2003/0135246 A1 | 7/2003 | Mass et al. |
| 2004/0034392 A1 | 2/2004 | Spadgenske et al. |
| 2005/0118887 A1 | 6/2005 | Hoffer et al. |
| 2006/0167522 A1 | 7/2006 | Malinowski |
| 2006/0199432 A1 | 9/2006 | Taylor et al. |
| 2007/0055319 A1 | 3/2007 | Spadgenske et al. |
| 2009/0243756 A1 | 10/2009 | Stevenson et al. |
| 2010/0331883 A1 | 12/2010 | Schmitz et al. |
| 2011/0022100 A1* | 1/2011 | Brase et al. ................ 607/2 |
| 2011/0301665 A1 | 12/2011 | Mercanzini et al. |
| 2012/0095529 A1 | 4/2012 | Parramon et al. |
| 2012/0221074 A1 | 8/2012 | Funderburk et al. |
| 2012/0262250 A1 | 10/2012 | Stevenson et al. |
| 2012/0283806 A1 | 11/2012 | Troosters et al. |
| 2013/0123866 A1 | 5/2013 | McDonald |
| 2014/0067020 A1 | 3/2014 | Kaula et al. |
| 2014/0107709 A1 | 4/2014 | Schmitz et al. |

\* cited by examiner

NEUROSTIMULATOR INTERCONNECTION APPARATUS, SYSTEM, AND METHOD

CROSS REFERENCE TO RELATED APPLICATIONS

This application claims the benefit of priority to U.S. Provisional Application Ser. No. 61/841,965, filed on Jul. 2, 2013, entitled "STIMULATION APPARATUSES, DEVICES, SYSTEMS, AND METHODS," which is incorporated by reference herein in its entirety.

TECHNICAL FIELD

The present patent document pertains generally to an interconnection apparatus, system, and method and more particularly, but not by way of limitation, to an interconnection apparatus, system, and method for use with a neurostimulation device.

BACKGROUND

Implantable neurostimulators are an emerging area of healthcare. Advances in microelectronics, rechargeable power sources, and high-density mechanical systems have led to smaller, more robust, and cost-effective componentry for implantable devices. Stimulating lead technology has also improved, allowing for large numbers of contacts to be positioned near neural targets to improve selective activation and individually tailor therapy.

Lead connector technology, however, remains expensive and bulky compared to the other advanced components in neurostimulator systems. Most of the cost of present-day multicontact neurostimulator is associated with lead connectors, and their size and volume limit package shape and shrinkability.

OVERVIEW

This overview is intended to provide an overview of subject matter of the present patent document. It is not intended to provide an exclusive or exhaustive explanation of the invention. The detailed description is included to provide further information about the present patent document.

The present inventor has recognized, among other things, that the subject matter can be used to couple components of a medical device. The present inventor has further recognized, among other things, that the subject matter can be used by an implantable stimulation system to couple a lead to a stimulator device. The present inventor further recognizes that achieving scalability of the subject matter to various sizes can mitigate problems with present day solutions. To better illustrate the apparatuses, systems, and methods described herein, a non-limiting list of examples is provided here:

Example 1 can include subject matter that can include neurostimulation interconnection apparatus including a substrate disposed within a header of a neurostimulation device. A spring contact is mounted to the substrate. The spring contact is oriented to accept and apply a clamping force to a proximal contact of a lead body to electrically couple the proximal contact of the lead body with the spring contact with insertion of the proximal contact within the spring contact. A trace is disposed on the substrate from the spring contact to a pin of a feedthrough of the neurostimulation device. The trace electrically couples the spring contact with the pin of the feedthrough.

In Example 2, the subject matter of Example 1 is optionally configured such that the substrate includes a printed circuit board.

In Example 3, the subject matter of any one of Examples 1-2 is optionally configured such that the spring contact includes a single-piece spring contact.

In Example 4, the subject matter of any one of Examples 1-3 is optionally configured such that the spring contact includes a multiple-piece spring contact.

In Example 5, the subject matter of any one of Examples 1-4 is optionally configured such that the spring contact includes a leaf spring contact.

In Example 6, the subject matter of Example 5 is optionally configured such that the leaf spring contact includes a stamped leaf spring contact.

In Example 7, the subject matter of any one of Examples 1-6 is optionally configured such that the spring contact includes a coiled spring contact.

In Example 8, the subject matter of any one of Examples 1-7 is optionally configured such that the substrate includes two or more spring contacts mounted to the substrate.

In Example 9, the subject matter of Example 8 is optionally configured such that the two or more spring contacts are oriented on the substrate in line with one another and are spaced to accommodate a corresponding two or more proximal contacts of the lead body to electrically couple the two or more proximal contacts of the lead body with the two or more spring contacts with insertion of the two or more proximal contacts within the two or more spring contacts.

In Example 10, the subject matter of any one of Examples 1-9 is optionally configured such that the substrate includes a plurality of spring contacts mounted to the substrate in line with one another. The plurality of spring contacts is spaced to accommodate and electrically couple to a corresponding plurality of proximal contacts of the lead body.

Example 11 can include, or can optionally be combined with any one of Examples 1-10 to include subject matter that can include a neurostimulation interconnection apparatus including a printed circuit board disposed within a header of a neurostimulation device. The printed circuit board includes a plurality of contact mounts. A plurality of traces is disposed on the printed circuit board. Each of the traces extend from one of the contact mounts to a pin of a feedthrough of the neurostimulation device. A plurality of spring contacts is mounted to the printed circuit board. Each of the spring contacts is mounted to one of the contact mounts of the printed circuit board. The spring contacts are oriented to accept and apply a clamping force to a corresponding number of proximal contacts of a lead body to electrically couple the proximal contacts of the lead body with the spring contacts with insertion of the proximal contacts within the spring contacts, and, in turn electrically couple each of the spring contacts with one of the pins of the feedthrough.

In Example 12, the subject matter of Example 11 is optionally configured such that each of the spring contacts includes a single-piece spring contact.

In Example 13, the subject matter of any one of Examples 11-12 is optionally configured such that each of the spring contacts includes a multiple-piece spring contact.

In Example 14, the subject matter of any one of Examples 11-13 is optionally configured such that each of the spring contacts includes a leaf spring contact.

In Example 15, the subject matter of Example 14 is optionally configured such that each of the leaf spring contacts includes a stamped leaf spring contact.

In Example 16, the subject matter of any one of Examples 11-15 is optionally configured such that each of the spring contacts includes a coiled spring contact.

In Example 17, the subject matter of any one of Examples 11-16 is optionally configured such that the spring contacts are mounted on the printed circuit board substantially in-line with one another. The plurality of spring contacts are spaced, such that, with insertion of the proximal contacts within the spring contacts, each of the plurality of spring contacts is aligned with a corresponding one of the plurality of proximal contacts.

Example 18 can include, or can optionally be combined with any one of Examples 1-17 to include subject matter that can include a neurostimulation interconnection apparatus including a substrate disposed within a header of a neurostimulation device. The substrate includes a plurality of contact mounts. There are a plurality of traces, each of the traces extending along the substrate from one of the contact mounts to a pin of a feedthrough of the neurostimulation device. There are a plurality of spring contacts, each of the spring contacts mounted to one of the contact mounts of the substrate. The spring contacts are oriented to accept and apply a clamping force to a corresponding number of proximal contacts of a lead body to electrically couple the proximal contacts of the lead body with the spring contacts with insertion of the proximal contacts within the spring contacts, and, in turn electrically couple each of the spring contacts with one of the pins of the feedthrough.

In Example 19, the subject matter of Example 18 is optionally configured such that each of the spring contacts includes a leaf spring contact.

In Example 20, the subject matter of any one of Examples 18-19 is optionally configured such that each of the spring contacts includes a coiled spring contact.

DETAILED DESCRIPTION

Figure 1:
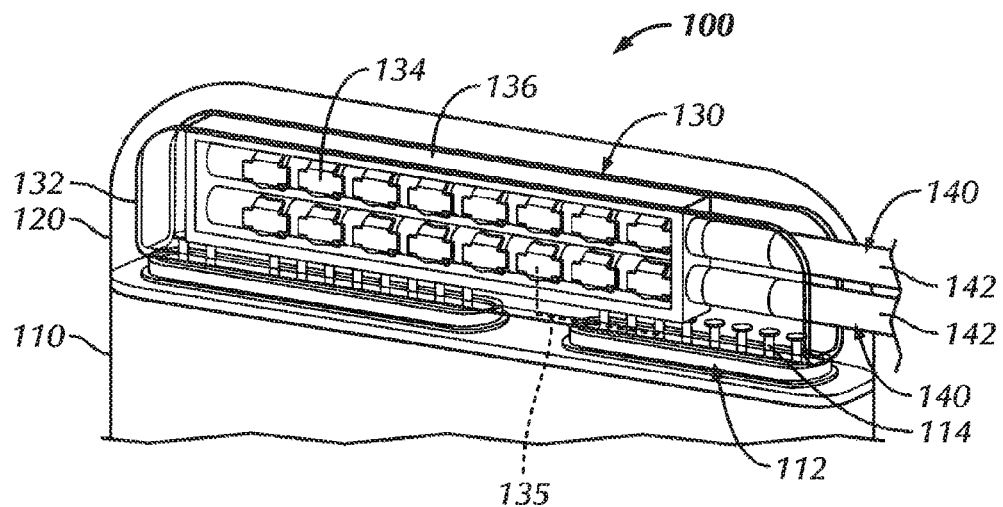
FIG. 1 shows an interconnection apparatus in accordance with at least one example of the invention.

The present patent document relates to apparatuses, systems, and methods for interconnecting components of an implantable device. In some examples, the apparatuses, systems, and methods described herein relate to interconnecting components of a neurostimulation device. For instance, the apparatuses, systems, and methods of the present patent document are used, in some examples, to interconnect one or more lead bodies with a stimulation device.

The present inventor has recognized, among other things, that it is desirable to provide an interconnection apparatus or system for a stimulation system, for instance, that is relatively low cost and reduced in size compared to existing interconnection systems. The present inventor has further recognized, among other things, that it is desirable to have a relatively easily manufacturable interconnection apparatus and system. The present inventor has recognized, among other things, that it is desirable to provide an interconnection apparatus or system for a stimulation system, for instance, that provides reduced sensitivity to misalignment, tool-less assembly, facilitated symmetric contact to iso-diametric leads, material flexibility, and/or easier scalability to better control of forces from all directions, to name a few. While primarily described with respect to neurostimulation devices, it should be understood, however, that the subject matter described herein can be used with other implantable medical devices, as well as external devices in some examples.

Various embodiments address a need for a low cost lead interconnection system for use in conjunction with a neuromodulator and/or neurostimulator device. Typically, such devices include a captive coiled spring connector assembly, which is relatively costly.

In some embodiments, the interconnection apparatuses, systems, and methods include a percutaneous lead with annular metallic contacts and a pulse generator with a corresponding contact array. In some embodiments, the pulse generator contacts maintain electrical continuity by exerting a clamping force on the percutaneous lead contacts. In some embodiments, the pulse generator utilizes contacts that are manufactured using low-cost standard manufacturing processes.

Referring to FIGS. 1-4B, in some embodiments, the interconnection apparatuses, systems, and methods described herein can include leaf-spring or coiled-spring contacts that are manufactured using processes such as metal stamping and wire forming. In some embodiments, proximal electrodes on the lead body are configured to connect to an implantable pulse generator (IPG) via spring-loaded or spring-based contacts. In some embodiments, the contacts are mounted to a PCB substrate or other substrate such that they are positioned in a linear array with spacing that aligns with the lead contacts. In some embodiments, the IPG contacts exert a clamping force on the lead contacts by means of a leaf spring or coiled spring configuration. In some embodiments, the PCB provides a direct lead path to the feedthrough pins.

Figure 2A:
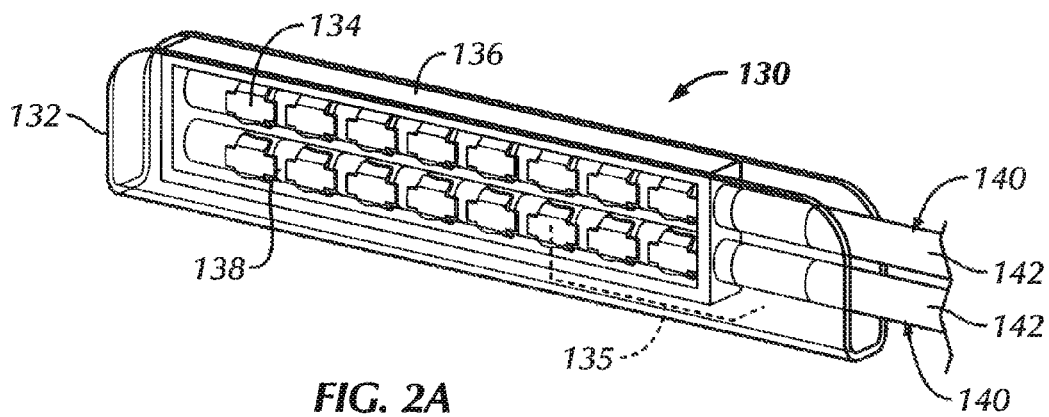
FIG. 2A shows a perspective view of an interconnection apparatus in accordance with at least one example of the invention.
Figure 2B:
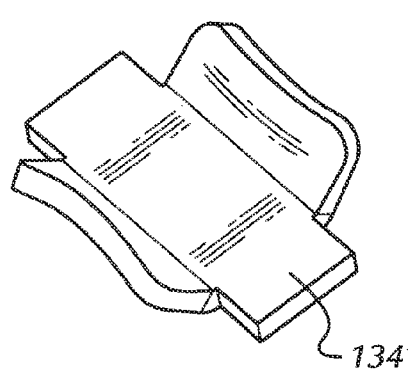
FIG. 2B shows a contact of the interconnection apparatus of FIG. 2A.
Figure 2C:
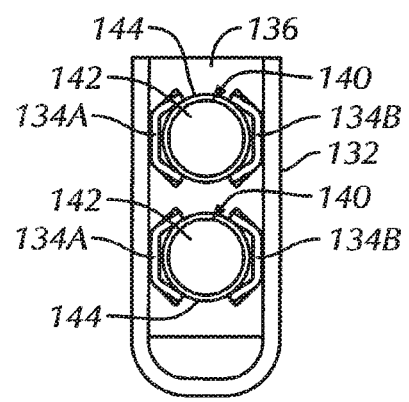
FIG. 2C shows a cross-sectional view of the interconnection apparatus of FIG. 2A.

Referring to FIGS. 1-2C, in some examples, a device 100, such as, for instance, a neurostimulation device 100, includes a device housing 110 and a header 120 attached to the device housing 110. In some examples, the device 100 includes a feedthrough 112 configured to couple electronic components within the device 110 with one or more components outside of the device housing 110. In some examples, the header 112 is configured to accept one or more apparatuses 140, such as, for instance, stimulation leads 140. In some examples, the device 100 can be used to perform nerve stimulation, for instance, to treat chronic pain, among other indications. In some examples, the device 100 is configured for use in peripheral nerve stimulation (PNS).

In some examples, the device 100 includes a neurostimulation interconnection apparatus 130. In some examples, the neurostimulation interconnection apparatus 130 is configured for connection of the one or more leads 140 to the device 100 and enabling electrical coupling of one or more distal electrodes of the one or more leads 140 to electronic components within the device housing 110 of the device 100. In some examples, the neurostimulation interconnection apparatus 130 is configured to electrically couple to one or more proximal contacts 144 disposed on a lead body 142 of the one or more leads 140.

In some examples, the neurostimulation interconnection apparatus 130 includes a substrate 132 disposed within the header 120 of the neurostimulation device 100. In some examples, the substrate 132 includes a printed circuit board. In further examples, the substrate 132 includes a flex circuit. In still further examples, the substrate 132 includes a ceramic substrate, polyimide with or without thin film, or the like. In some examples, the interconnection apparatus 130 includes a spring contact 134 mounted to the substrate 132. In some examples, the spring contact 134 is oriented to accept and apply a clamping force to one of the one or more proximal contacts 144 of the lead body 142 to electrically couple the proximal contact 144 of the lead body 142 with the spring contact 134 with insertion of the proximal contact 144 within the spring contact 134. In some examples, the spring contact 134 is configured to apply a substantially symmetric clamping force to one of the one or more proximal contacts 144 of the lead body 142. In some examples, substantially symmetric clamping force can provide reduced sensitivity to misalignment, reduced insertion force, and facilitated symmetric contact, to name a few. In some examples, the spring contact 134 includes a multiple-piece spring contact. For instance, referring briefly to FIG. 2C, in some examples, the spring contact 134 includes two spring contacts 134A, 134B disposed on opposite sides from one another so as to contact opposite sides of the proximal contact 144 of the lead 140. In some examples, the substrate 132 is disposed on both sides of the lead 140, with one spring contact 134A disposed on the substrate 132 on one side and the other spring contact 134B on the other side. In some examples, the substrate 132 is formed or flexed into a U shape. In some examples, the spring contact 134 includes a leaf spring contact. In some examples, the leaf spring contact includes a stamped leaf spring contact. In some examples, the spring contact 134 is formed from metal.

In some examples, the substrate 132 includes two or more spring contacts 134 mounted to the substrate 132. In some examples, the two or more spring contacts 134 are mounted to contact mounts disposed in the substrate 132. In some examples, the spring contacts 134 are spot welded or otherwise attached with the contact mounts. In some examples, the contact mounts are holes or other formations drilled or otherwise formed in the substrate 132. In some examples, the holes or other formations can be precisely formed in the substrate 132 to allow for proper placement of the spring contacts 134 with respect to the substrate 132 and, in turn, with respect to the header 120. In some examples, the two or more spring contacts 134 are oriented on the substrate 132 in line with one another and are spaced to accommodate a corresponding two or more proximal contacts 144 of the lead body 142 to electrically couple the two or more proximal contacts 144 of the lead body 142 with the two or more spring contacts 134 with insertion of the two or more proximal contacts 144 within the two or more spring contacts 134.

In some examples, the substrate 132 includes a plurality of spring contacts 134 mounted to the substrate 132 in line with one another. In some examples, the plurality of spring contacts 134 is spaced to accommodate and electrically couple to a corresponding plurality of proximal contacts 144 of the lead body 142. In some examples, the spring contacts 134 are aligned along a bore of the header 120 within which the lead 140 can be at least partially inserted. In some examples, the spring contacts 134 are aligned along two or more bores of the header 120 within which two or more leads 140 can be at least partially inserted. In some examples, a seal 138 is disposed between adjacent spring contacts 134 along the bore in order to electrically isolate each spring contact 134 from one or more adjacent spring contacts 134 and inhibit outside substances (body fluids, for instance) from entering the bore of the header 120 and/or coming into contact with the spring contacts 134. In some examples, the interconnection apparatus 130 includes a frame 136, for instance to rigidify the interconnection apparatus 130 and, in turn, the header 120. In some examples, the frame 136 includes one or more set screws to allow for fastening of the one or more leads 140 within the bore of the header 120.

In some examples, a trace 135 is disposed on the substrate 132 from the spring contact 134 to a pin 114 of the feedthrough 112 of the neurostimulation device 100. In some examples, the trace 135 electrically couples the spring contact 134 with the pin 114 of the feedthrough 112. It is noted that only one trace 135 is shown in FIGS. 1 and 2A for ease of illustration. However, in some examples, a trace 135 would electrically couple each of the spring contacts 134 with a corresponding pin 114 of the feedthrough 112.

Figure 3A:
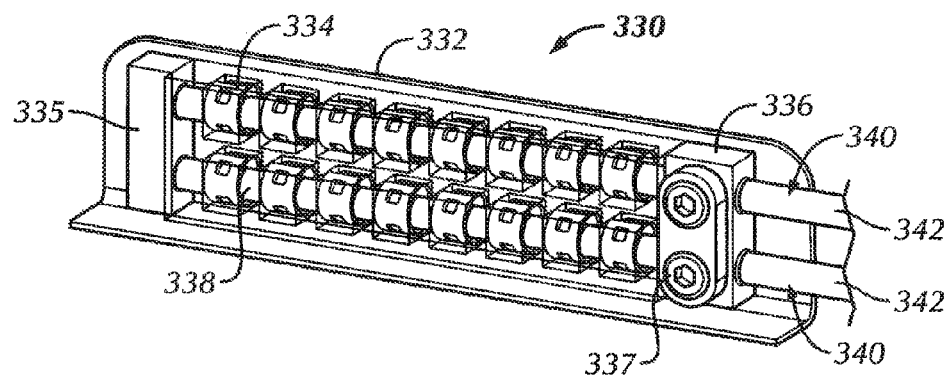
FIG. 3A shows an interconnection apparatus in accordance with at least one example of the invention.
Figure 3B:
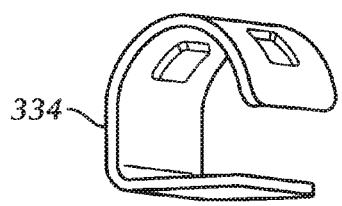
FIG. 3B shows a contact of the interconnection apparatus of FIG. 3A.

Referring to FIGS. 3A and 3B, in some examples, a neurostimulation interconnection apparatus 330 can be used in a device similar to the neurostimulation device 100 described herein. In some examples, the neurostimulation interconnection apparatus 330 is configured for connection of the one or more leads 340 to the device and enabling electrical coupling of one or more distal electrodes of the one or more leads 340 to electronic components within a device housing of the device. In some examples, the neurostimulation interconnection apparatus 330 is configured to electrically couple to one or more proximal contacts disposed on a lead body 342 of the one or more leads 340.

In some examples, the neurostimulation interconnection apparatus 330 includes a substrate 332 disposed within a header of the neurostimulation device. In some examples, the substrate 332 includes a printed circuit board. In further examples, the substrate 332 includes a flex circuit. In still further examples, the substrate 332 includes a ceramic substrate, polyimide with or without thin film, or the like. In some examples, the interconnection apparatus 330 includes a spring contact 334 mounted to the substrate 332. In some examples, the spring contact 334 is oriented to accept and apply a clamping force to one of the one or more proximal contacts of the lead body 342 to electrically couple the proximal contact of the lead body 342 with the spring contact 334 with insertion of the proximal contact within the spring contact 334. In some examples, the spring contact 334 is configured to apply a substantially symmetric clamping force to one of the one or more proximal contacts of the lead body. In some examples, substantially symmetric clamping force can provide reduced sensitivity to misalignment, reduced insertion force, and facilitated symmetric contact, to name a few. In some examples, the spring contact 334 includes a single-piece spring contact. In some examples, the spring contact 334 is configured to extend more than halfway around the circumference of the lead body 342. In some examples, the substrate 332 is formed or flexed into an L shape. In some examples, the spring contact 334 includes a leaf spring contact. In some examples, the leaf spring contact includes a stamped leaf spring contact. In some examples, the spring contact 334 is formed from metal.

In some examples, the substrate 332 includes two or more spring contacts 334 mounted to the substrate 332. In some examples, the two or more spring contacts 334 are mounted to contact mounts disposed in the substrate 332. In some examples, the spring contacts 334 are spot welded or otherwise attached with the contact mounts. In some examples, the contact mounts are holes or other formations drilled or otherwise formed in the substrate 332. In some examples, the holes or other formations can be precisely formed in the substrate 332 to allow for proper placement of the spring contacts 334 with respect to the substrate 332 and, in turn, with respect to the header. In some examples, the two or more spring contacts 334 are oriented on the substrate 332 in line with one another and are spaced to accommodate a corresponding two or more proximal contacts of the lead body 342 to electrically couple the two or more proximal contacts of the lead body 342 with the two or more spring contacts 334 with insertion of the two or more proximal contacts within the two or more spring contacts 334.

In some examples, the substrate 332 includes a plurality of spring contacts 334 mounted to the substrate 332 in line with one another. In some examples, the plurality of spring contacts 334 is spaced to accommodate and electrically couple to a corresponding plurality of proximal contacts of the lead body 342. In some examples, the spring contacts 334 are aligned along a bore of the header within which the lead 340 can be at least partially inserted. In some examples, the spring contacts 334 are aligned along two or more bores of the header within which two or more leads 340 can be at least partially inserted. In some examples, a seal 338 is disposed between adjacent spring contacts 334 along the bore in order to electrically isolate each spring contact 334 from one or more adjacent spring contacts 334 and inhibit outside substances (body fluids, for instance) from entering the bore of the header and/or coming into contact with the spring contacts 334. In some examples, the interconnection apparatus 330 includes an end cap 335 and a set screw block 336, for instance to rigidify the interconnection apparatus 330 and, in turn, the header. In some examples, the set screw block 336 includes one or more set screws 337 to allow for fastening of the one or more leads 340 within the bore of the header.

In some examples, a trace (for instance, similar to the trace 135 described herein with respect to the interconnection apparatus 130) is disposed on the substrate 332 from the spring contact 334 to a pin of the feedthrough of the neurostimulation device. In some examples, the trace electrically couples the spring contact 334 with the pin of the feedthrough. In some examples, a trace electrically couples each of the spring contacts 334 with a corresponding pin of the feedthrough.

Figure 4A:
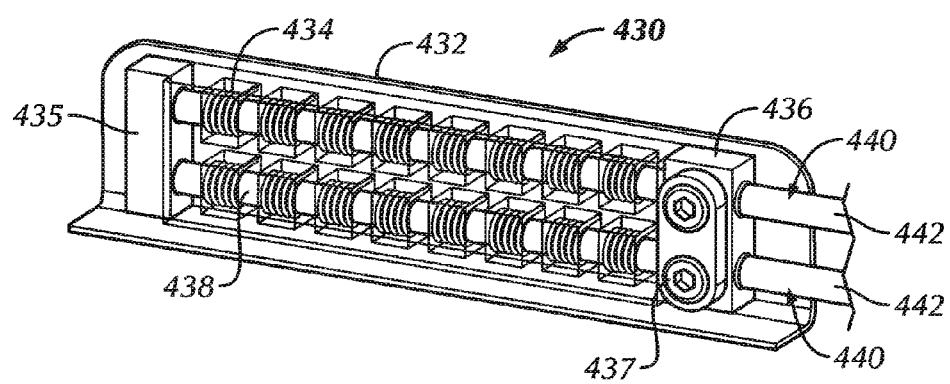
FIG. 4A shows an interconnection apparatus in accordance with at least one example of the invention.
Figure 4B:
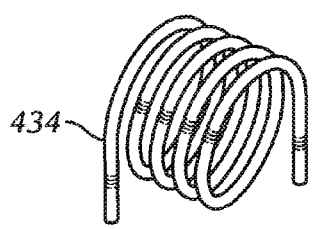
FIG. 4B shows a contact of the interconnection apparatus of FIG. 4A.

Referring to FIGS. 4A and 4B, in some examples, a neurostimulation interconnection apparatus 430 can be used in a device similar to the neurostimulation device 100 described herein. In some examples, the neurostimulation interconnection apparatus 430 is configured for connection of the one or more leads 440 to the device and enabling electrical coupling of one or more distal electrodes of the one or more leads 440 to electronic components within a device housing of the device. In some examples, the neurostimulation interconnection apparatus 430 is configured to electrically couple to one or more proximal contacts disposed on a lead body 442 of the one or more leads 440.

In some examples, the neurostimulation interconnection apparatus 430 includes a substrate 432 disposed within a header of the neurostimulation device. In some examples, the substrate 432 includes a printed circuit board. In further examples, the substrate 432 includes a flex circuit. In still further examples, the substrate 432 includes a ceramic substrate, polyimide with or without thin film, or the like. In some examples, the interconnection apparatus 430 includes a spring contact 434 mounted to the substrate 432. In some examples, the spring contact 434 is oriented to accept and apply a clamping force to one of the one or more proximal contacts of the lead body 442 to electrically couple the proximal contact of the lead body 442 with the spring contact 434 with insertion of the proximal contact within the spring contact 434. In some examples, the spring contact 434 is configured to apply a substantially symmetric clamping force to one of the one or more proximal contacts of the lead body. In some examples, substantially symmetric clamping force can provide reduced sensitivity to misalignment, reduced insertion force, and facilitated symmetric contact, to name a few. In some examples, the spring contact 434 includes a single-piece spring contact. In some examples, the spring contact 434 includes a coiled spring contact. In some examples, the spring contact 434 is configured to extend more than halfway around the circumference of the lead body 442. In some examples, the substrate 432 is formed or flexed into an L shape. In some examples, the spring contact 434 is formed from metal.

In some examples, the substrate 432 includes two or more spring contacts 434 mounted to the substrate 432. In some examples, the two or more spring contacts 434 are mounted to contact mounts disposed in the substrate 432. In some examples, the spring contacts 434 are spot welded or otherwise attached with the contact mounts. In some examples, the contact mounts are holes or other formations drilled or otherwise formed in the substrate 432. In some examples, the holes or other formations can be precisely formed in the substrate 432 to allow for proper placement of the spring contacts 434 with respect to the substrate 432 and, in turn, with respect to the header. In some examples, the two or more spring contacts 434 are oriented on the substrate 432 in line with one another and are spaced to accommodate a corresponding two or more proximal contacts of the lead body 442 to electrically couple the two or more proximal contacts of the lead body 442 with the two or more spring contacts 434 with insertion of the two or more proximal contacts within the two or more spring contacts 434.

In some examples, the substrate 432 includes a plurality of spring contacts 434 mounted to the substrate 432 in line with one another. In some examples, the plurality of spring contacts 434 is spaced to accommodate and electrically couple to a corresponding plurality of proximal contacts of the lead body 442. In some examples, the spring contacts 434 are aligned along a bore of the header within which the lead 440 can be at least partially inserted. In some examples, the spring contacts 434 are aligned along two or more bores of the header within which two or more leads 440 can be at least partially inserted. In some examples, a seal 438 is disposed between adjacent spring contacts 434 along the bore in order to electrically isolate each spring contact 434 from one or more adjacent spring contacts 434 and inhibit outside substances (body fluids, for instance) from entering the bore of the header and/or coming into contact with the spring contacts 434. In some examples, the interconnection apparatus 430 includes an end cap 435 and a set screw block 436, for instance to rigidify the interconnection apparatus 430 and, in turn, the header. In some examples, the set screw block 436 includes one or more set screws 437 to allow for fastening of the one or more leads 440 within the bore of the header.

In some examples, a trace (for instance, similar to the trace 135 described herein with respect to the interconnection apparatus 130) is disposed on the substrate 432 from the spring contact 434 to a pin of the feedthrough of the neurostimulation device. In some examples, the trace electrically couples the spring contact 434 with the pin of the feedthrough. In some examples, a trace electrically couples each of the spring contacts 434 with a corresponding pin of the feedthrough.

In various examples, the spring contacts 134, 334, 434 allow for a more tunable and/or predictable clamping force around the respective lead bodies 142, 342, 442, and, in turn more predictable insertion force prediction for inserting the respective lead bodies 142, 342, 442 within the header 120. In some examples, use of the substrate 132, 332, 432 (a PCB, for instance) allows pre-forming or pre-cutting of the contact mounts to facilitate more accurate and/or more reproducible alignment and spacing of the spring contacts 134, 334, 434. In some examples, the formation or cutting of the contact mounts can be automated.

The interconnection apparatuses and systems according to the various embodiments can include reduced cost, reduced size, simplified manufacturing, and the use of existing leads. Features or elements of the various embodiments can include stamped or wireform contacts (e.g., platinum iridium), a flex polyimide printed circuit board (PCB) with PI traces—no wires, contacts spot welded to PCB, and/or silicone injected for seal and insulation. Benefits of the various embodiments can include cost reduction; size reduction—for instance, approximately 25% less volume; manufacturing simplified—no individual wires, contacts are spot welded, for instance, in an automated process; and/or compatibility with existing leads. The various embodiments can include various contact options taking insertion force and manufacturability into account, header casting processes, silicone injection for sealing around contacts, and/or spot welding processes.

The present inventor has recognized various advantages of the subject matter described herein. For instance, in some examples, the apparatuses, systems, and methods described herein are considered advantageous in that they allow for relatively low cost and relatively small interconnection of lead bodies and stimulation devices. Additionally, in various examples, the apparatuses, systems, and methods described herein are considered advantageous by providing a relatively easily manufacturable interconnection apparatus and system. The present inventor has further recognized that, in some examples, the apparatuses, systems, and methods described herein are considered advantageous in that they provide for reduced sensitivity to misalignment, tool-less assembly, facilitated symmetric contact to iso-diametric leads, material flexibility, and/or easier scalability to better control of forces from all directions, to name a few. While various advantages of the example apparatuses, systems, and methods are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A neurostimulation interconnection apparatus comprising:
   a substrate disposed within a header of a neurostimulation device;
   a spring contact mounted directly to the substrate, the spring contact being oriented on the substrate to accept and apply a clamping force to a proximal contact of a lead body to electrically couple the proximal contact of the lead body with the spring contact upon insertion of the proximal contact within the spring contact; and
   a trace disposed on the substrate from the spring contact to a pin of a feedthrough of the neurostimulation device, the trace electrically coupling the spring contact with the pin of the feedthrough.

2. The neurostimulation interconnection apparatus of claim 1, wherein the substrate includes a printed circuit board.

3. The neurostimulation interconnection apparatus of claim 1, wherein the spring contact includes a single-piece spring contact.

4. The neurostimulation interconnection apparatus of claim 1, wherein the spring contact includes a multiple-piece spring contact.

5. The neurostimulation interconnection apparatus of claim 1, wherein the spring contact includes a leaf spring contact.

6. The neurostimulation interconnection apparatus of claim 5, wherein the leaf spring contact includes a stamped leaf spring contact.

7. The neurostimulation interconnection apparatus of claim 1, wherein the spring contact includes a coiled spring contact.

8. The neurostimulation interconnection apparatus of claim 1, wherein the substrate includes two or more spring contacts mounted to the substrate.

9. The neurostimulation interconnection apparatus of claim 8, wherein the two or more spring contacts are oriented on the substrate in line with one another and are spaced to accommodate a corresponding two or more proximal contacts of the lead body to electrically couple the two or more proximal contacts of the lead body with the two or more spring contacts with insertion of the two or more proximal contacts within the two or more spring contacts.

10. The neurostimulation interconnection apparatus of claim 1, wherein the substrate includes a plurality of spring contacts mounted to the substrate in line with one another, the plurality of spring contacts being spaced to accommodate and electrically couple to a corresponding plurality of proximal contacts of the lead body.

11. A neurostimulation interconnection apparatus comprising:
- a printed circuit board disposed within a header of a neurostimulation device, the printed circuit board including a plurality of contact mounts;
- a plurality of traces disposed on the printed circuit board, each of the traces extending from one of the contact mounts to a pin of a feedthrough of the neurostimulation device; and
- a plurality of spring contacts, each of the spring contacts directly mounted to one of the contact mounts of the printed circuit board, the spring contacts being oriented on the substrate to accept and apply a clamping force to a corresponding number of proximal contacts of a lead body to electrically couple the proximal contacts of the lead body with the spring contacts upon insertion of the proximal contacts within the spring contacts, and, in turn electrically couple each of the spring contacts with one of the pins of the feedthrough.

12. The neurostimulation interconnection apparatus of claim 11, wherein each of the spring contacts includes a single-piece spring contact.

13. The neurostimulation interconnection apparatus of claim 11, wherein each of the spring contacts includes a multiple-piece spring contact.

14. The neurostimulation interconnection apparatus of claim 11, wherein each of the spring contacts includes a leaf spring contact.

15. The neurostimulation interconnection apparatus of claim 14, wherein each of the leaf spring contacts includes a stamped leaf spring contact.

16. The neurostimulation interconnection apparatus of claim 11, wherein each of the spring contacts includes a coiled spring contact.

17. The neurostimulation interconnection apparatus of claim 11, wherein the spring contacts are mounted on the printed circuit board substantially in-line with one another, the plurality of spring contacts being spaced, such that, with insertion of the proximal contacts within the spring contacts, each of the plurality of spring contacts is aligned with a corresponding one of the plurality of proximal contacts.

18. A neurostimulation interconnection apparatus comprising:
- a substrate disposed within a header of a neurostimulation device, the substrate including a plurality of contact mounts;
- a plurality of traces, each of the traces extending along the substrate from one of the contact mounts to a pin of a feedthrough of the neurostimulation device; and
- a plurality of spring contacts, each of the spring contacts mounted directly to one of the contact mounts of the substrate, the spring contacts being oriented on the substrate to accept and apply a clamping force to a corresponding number of proximal contacts of a lead body to electrically couple the proximal contacts of the lead body with the spring contacts upon insertion of the proximal contacts within the spring contacts, and, in turn electrically couple each of the spring contacts with one of the pins of the feedthrough.

19. The neurostimulation interconnection apparatus of claim 18, wherein each of the spring contacts includes a leaf spring contact.

20. The neurostimulation interconnection apparatus of claim 18, wherein each of the spring contacts includes a coiled spring contact.

* * * * *